US007074391B1

(12) United States Patent
Alvarez Hernandez

(10) Patent No.: US 7,074,391 B1
(45) Date of Patent: Jul. 11, 2006

(54) USE OF OLIVE OIL IN THE PREPARATION OF A PRODUCT FOR ORAL HYGIENE FOR ELIMINATING OR REDUCING BACTERIAL PLAQUE AND/OR BACTERIA IN THE MOUTH

(75) Inventor: Maria Alvarez Hernandez, Madrid (ES)

(73) Assignee: Biocosmetics, S.L. (ES)

( * ) Notice: Subject to any disclaimer, the term of this patent is extended or adjusted under 35 U.S.C. 154(b) by 58 days.

(21) Appl. No.: 10/399,459

(22) PCT Filed: Oct. 16, 2000

(86) PCT No.: PCT/ES00/00397

§ 371 (c)(1),
(2), (4) Date: Nov. 24, 2003

(87) PCT Pub. No.: WO02/32387

PCT Pub. Date: Apr. 25, 2002

(51) Int. Cl.
*A61K 7/16* (2006.01)
*A61K 7/18* (2006.01)
*A61K 35/78* (2006.01)
*A61K 33/00* (2006.01)
*A61K 31/045* (2006.01)

(52) U.S. Cl. ............................. 424/49; 424/52; 424/58; 424/722; 424/777; 514/724

(58) Field of Classification Search ................ 429/49, 429/78, 777, 722, 405; 514/724
See application file for complete search history.

(56) References Cited

U.S. PATENT DOCUMENTS 3,967,563 A * 7/1976 Wason ..................... 106/492

| 4,525,342 A | | 6/1985 | Weiss et al. |
| 4,894,220 A | | 1/1990 | Nabi et al. |
| 5,089,255 A | * | 2/1992 | Gaffar et al. ................. 424/52 |
| 5,130,122 A | | 7/1992 | Tabibi et al. |
| 5,733,530 A | * | 3/1998 | Bacca et al. ................. 424/52 |
| 5,899,168 A | * | 5/1999 | Rojas et al. ................. 119/6.5 |
| 6,342,206 B1 | * | 1/2002 | Gopalkrishnan et al. ...... 424/49 |
| 6,358,542 B1 | * | 3/2002 | Cuomo et al. ............. 424/777 |

FOREIGN PATENT DOCUMENTS

| EP | 0251146 | | 1/1988 |
| EP | 1053743 | * | 6/1998 |
| EP | 2134743 | | 10/2001 |
| ES | 2063245 | | 1/1995 |
| GB | 2219937 | | 12/1989 |
| JP | 53-096337 | | 8/1978 |
| JP | 08310943 | * | 11/1996 |
| JP | 2001181161 | * | 7/2001 |

OTHER PUBLICATIONS

K. Yaegaki, et al., "Effects of Two-Phase Oil-Water Mouthwash on Halitosis", *Clinical Preventive Dentistry*, Jan.-Feb. 1992, vol. 14, No. 1, pp. 5-9.
Rieger, Martin M., Ph.D., "Harry's Cosmeticology" *Chemical Publishing Co., Inc.*, Eight Edition, New York., p. 732.

* cited by examiner

*Primary Examiner*—Christopher R. Tate
(74) *Attorney, Agent, or Firm*—Ostrolenk, Faber, Gerb & Soffen, LLP

(57) ABSTRACT

The use of olive oil is described in the preparation of a product intended for oral hygiene, for example, a toothpaste, a mouthwash, a spray or oral inhaler or chewing gum, to eliminate or to reduce the bacterial plaque and/or bacteria present in the buccal cavity, achieving thereby a reduction in the occurrence of dental diseases (tooth decay, periodontal disease) and halitosis.

5 Claims, No Drawings

USE OF OLIVE OIL IN THE PREPARATION OF A PRODUCT FOR ORAL HYGIENE FOR ELIMINATING OR REDUCING BACTERIAL PLAQUE AND/OR BACTERIA IN THE MOUTH

FIELD OF THE INVENTION

This invention refers, in general, to the employment of olive oil in the preparation of a product intended for oral hygiene to eliminate or to reduce the bacterial plaque and/or bacteria present in the buccal cavity.

BACKGROUND OF THE INVENTION

Bacterial plaque is a thin, colourless and sticky, almost invisible film that is being formed continually on the teeth, in the greater part, but also on the back of the tongue, palate, mucous membrane, vestibule and lips. It is composed of bacteria, saliva and remains of foodstuffs and it is the main cause of the 2 most common dental diseases: tooth decay and periodontal disease. Daily dental hygiene is essential for removing plaque and keeping the mouth healthy.

Tooth decay is a localised infectious process, of external origin, that causes the debilitation of the hard tissue (enamel) of the tooth and leads to the formation of a cavity. The main etiologic agent causing this dental disease seems to be the gram (+) bacteria Streptococcus mutans.

Periodontal disease is a disease that affects the gums and the structures supporting the teeth. The earliest stage in periodontal disease is gingivitis and it is characterized by a reddening of the gums that become inflamed and bleed easily. If the disease is not appropriately treated at that stage it can develop into periodontitis and cause irreversible damage to the gums. In periodontitis, the most advanced stage in periodontal disease, the bone and the tissue that surround the teeth are destroyed and pockets are formed in the gums that are filled with more bacterial plaque. As the disease progresses, the teeth become slack or loose and can eventually fall out or require extraction.

The main cause of periodontal disease is the bacterial plaque which, if it is not removed, hardens and builds up on the teeth. The toxins produced by the bacteria present in the bacterial plaque destroy supporting tissue around the teeth, the gums loosen and the teeth separate forming the pockets that are filled with bacterial plaque.

Periodontal disease can be prevented by removing the bacterial plaque by means of frequent and careful brushing and with the help of dental floss and, optionally, with the use of interdental or interproximal brushes, interdental stimulants and/or mouthwashes. However, daily cleaning is not sufficient and it should be completed with professional cleaning carried out by a dentist that will remove the hardened deposits that have been formed and could not be removed by daily brushing.

The usual treatment of periodontal disease consists of scraping, curettage and radicular planing, which implies removing the plaque and the calculus from the pockets around the teeth, polishing and planing the roots with the aim that the gum adheres again to the tooth or contracts enough to eliminate the pocket. However, the most advanced cases can require surgical treatment.

On the other hand, halitosis or bad breath, is a dysfunction caused by the production and liberation of diverse volatile compounds, mainly volatile sulphurated compounds (VSC), such as hydrogen sulphide and methyl mercaptan. The buccal cavity contains microorganisms, in general, anaerobic bacteria and gram (−) bacteria, responsible to a certain extent for the occurrence of halitosis. Diverse treatments exist to combat halitosis, some based on the administration of synthetic products while others are based on the administration of natural products [see Spanish patent application No. P9701545].

In spite of having diverse means to prevent and to treat bacterial plaque, and to treat halitosis, there continues to be a need to increase the arsenal of remedies for combating the formation of bacterial plaque and/or the presence of noxious microorganisms in the buccal cavity.

The present invention provides a solution for said existing necessity that consists in employing olive oil in the preparation of an oral hygiene product intended for eliminating or reducing the bacterial plaque and/or noxious bacteria present in the buccal cavity. As a consequence of this total or partial reduction of bacterial plaque and/or of the bacteria present in the buccal cavity, the occurrence is decreased of oral diseases, decay, periodontitis and its first stages (gingivitis), as well as halitosis associated with the production of VSC by microorganisms present in the buccal cavity.

Olive oil is a product habitually used in food although other therapeutic and cosmetic applications are also known [see Spanish patent application No. 9801543]. Oleic acid [cis-9-octadecenoic acid] is a monounsaturated fatty acid that seems to be the responsible for numerous beneficial effects of olive oil. It is very well known that oleic acid helps in the prevention of arteriosclerosis, increases the level of cholesterol connected with high density lipoproteins and reduces the level of cholesterol connected with low density lipoproteins, achieving in this way an appropriate manner of combating the occurrence of cardiovascular diseases.

Olive oil contains, also, vitamins (A, E, F and K) and polyphenols and it seems to be that the antioxidant substances present in olive oil (vitamins A and E and polyphenols) provide the organism with a defence mechanism that delays aging, prevents arteriosclerosis, the appearance of breast cancer, hepatic disorders and inflammation.

Olive oil is well tolerated by the stomach, has beneficial effects on gastritis and ulcers, is a cholagogue, activates the secretion of pancreatic hormones and bile, and diminishes the incidence of cholelythiasis. On the other hand, its excellent digestibility results in the complete absorption of nutritients, especially vitamins and mineral salts and it contributes the necessary oleates for the bone system. The mineralising effect that is exercised by olive oil is excellent both in childhood and when aging, a stage in which mineralisation problems usually appear.

Olive oil also has a beneficial effect on the brain and on the central nervous system, it protects the body against the occurrence of infections and assists in the healing of internal and external tissue.

Besides the aforementioned therapeutic indications, olive oil has cosmetic applications and at the moment it is beginning to be used as a skin protector, acting against the appearance of wrinkles and as a lotion for dry and scaly skins. It is also used to restore shine and vigour to damaged hair and eyelashes and to recover the vitality of fragile hair.

In the Mediterranean region olive oil is known for its capacity as a preservative and germicide (it is used to preserve fish, vegetables, cheese, etc.). In the case of such products as cheese or fish that can contain a great quantity of bacteria when initially immersed in olive oil, the bacteria count obtained is practically nil after a few hours from their immersion in olive oil.

It has been found that, surprisingly, olive oil can be used to reduce or to eliminate bacterial plaque and/or the bacteria present in the buccal cavity.

DETAILED DESCRIPTION OF THE INVENTION

The present invention refers to the employment of olive oil in the preparation of a product intended for oral hygiene to eliminate or reduce bacterial plaque and/or bacteria present in the buccal cavity.

In the sense used in this description, the expression " to eliminate or reduce bacterial plaque and/or bacteria present in the buccal cavity" means that bacterial plaque and/or bacteria present in the buccal cavity decrease totally or partially to levels at which (i) they do not give rise to the occurrence of dental disease, or (ii) they do not give rise to the release of VSC in a sufficient quantity for bad breath to be noticed (typically 75 ppb of said VSC).

Olive oil is a commercial product that is obtained by pressing olives, the fruit of the olive tree [*Olea europea* L.]. The olive oil that can be present in the product intended for oral hygiene to eliminate or reduce bacterial plaque and/or bacteria present in the buccal cavity, can be any olive oil, for example, a commercial olive oil, such as virgin olive oil, refined olive oil and olive oil (a blend of virgin and refined olive oils whose maximum acidity is 1° and the peroxide index of which is less than 15, preferably less than 10).

The product intended for oral hygiene can be any product that can be used in oral cleansing and/or disinfection and it can adopt any form of presentation, for example, toothpaste, mouthwash, oral spray or inhaler, chewing gum, etc.

For the development of the present invention it has been essential to analyse the properties of the microorganisms that are the cause of dental diseases and the production of VSC.

The analysis of the most frequently isolated microorganisms in bacterial plaque has shown the presence of numerous lipophile microorganisms, understanding such to be those microorganisms whose cellular coat is rich in lipids or substances that have an affinity for lipids, for example, *Actinobacillus actinomycetemcomitans, Actinomyces viscosus, Actinomyces naeslundii, Porphyromonas gingivalis, Streptococcus salivarus, Streptococcus sanguis* and *Streptococcus mutans*, some of which are responsible for the production of VSC and of periodontitis while others, mainly *S. mutans*, are those responsible for the occurrence of caries.

Also, the identification of the bacterial species associated with periodontal disease is a key aspect for the diagnosis and tracking of the disease. The most frequently identified periodontal pathogens are *Porphyromonas gingivalis, Prevotella intermedia, Actinobacillus actinomycetem-comitans, Fusobacterium nucleatum, Eikenella corrodens, Bacteroides frosythus, Capnocytophaga spp.* In short, the following have been identified:

in association with periodontitis in adults: *Actinobacillus actinomycetemcomitans, Porphyromonas gingivalis, Bacteroides frosythus, Prevotella intermedia* and *Eikenella corrodens*;

in association with prepubertal periodontitis: *Actinobacillus actinomycetemcomitans* and *Capnocytophaga* spp.;

in association with juvenile periodontitis: *Actinobacillus actinomycetemcomitans, Porphyromonas gingivalis,* and *Prevotella intermedia*; and in association with rapid progressive periodontitis: *Actinobacillus actinomycetemcomitans, Eikenella corrodens* and *Bacteroides frosythus.*

A common property of the bacteria mentioned previously as responsible for periodontal disease is that they are gram-negative [gram (−)] bacteria when submitted to staining with crystal violet.

Numerous trials carried out with diverse products showed that, surprisingly, olive oil was a specially appropriate product for reducing or eliminating bacterial plaque and/or the bacteria present in the buccal cavity, some of them responsible for the occurrence of cavities and others for the production of VSC, a significant improvement being obtained in this way in dental health due to a reduction in the occurrence of gingivitis and periodontitis and tooth decay, as well as a reduction of halitosis due to the production of VSC.

Various trials showed that olive oil can act as a bacteriostatic in formulas of products for oral hygiene with an average content of olive oil, typically 1% to 60% by weight with respect to the total of the formula, or as a germicide in formulas of products for oral hygiene with a high content of olive oil, typically 15% to 70% by weight with respect to the total of the formula. It can be observed that, in certain concentrations, olive oil can act well as a bacteriostatic or as a bactericide.

There has been surprise at the unusual and astonishing capacity of olive oil, that constitutes the essential object of this invention, to reduce totally or partially the population of bacteria present in the buccal cavity and/or in bacterial plaque, fundamentally, anaerobic and gram (−) bacteria, microorganisms that cause the occurrence of dental diseases and halitosis.

Although there is no wish to be bound to any particular theory, it seems that the high content in lipids of the cellular wall of the gram (−) bacteria make said walls hydrophobic and capable of being dissolved in a lipid medium. This reason could explain why a medium rich in oils is more effective when eliminating gram (−) bacteria than an aqueous medium. It seems that the gram (−) bacteria have greater affinity for olive oil than for the aqueous medium of the saliva whereby they would adhere to or be trapped in the oil and would be eliminated together with this by rinsing the mouth.

The employment of olive oil in the preparation of a product intended for oral hygiene to eliminate or reduce bacterial plaque and/or bacteria present in the buccal cavity contributes numerous advantages, such as:

providing good cleansing, not abrasive, of the cavity and teeth carrying off the lipophilic microorganisms;

reducing the absolute quantity of bacterial plaque both supra—and infra-gingival with a significant improvement in the periodontal health (reduction of cavities, gingivitis and improvement in periodontitis); and reducing the occurrence of halitosis by reducing the quantity of VSC arising from the microorganisms that produce VSC by blocking or inactivating these microorganisms and/or by neutralising the VSC, once emitted by the producing microorganisms, so that they are not detected by smell.

The invention also provides a product for oral hygiene appropriate for eliminating or reducing bacterial plaque and/or bacteria present in the buccal cavity that contains olive oil, hereafter product for oral hygiene of the invention. Preferably, olive oil is present in the product for oral hygiene of the invention in a quantity of between 1% and 70% by weight with respect to the total of the product.

The product for oral hygiene of the invention can adopt any form of presentation, for example, toothpaste, mouthwash, oral spray or inhaler, chewing gum, etc., for which its formula will include the components, additives and appropriate vehicles for its form of presentation.

By way of illustration, when the product for oral hygiene of the invention is presented in the form of a toothpaste, this can contain, besides the olive oil, other compounds that furnish some special property thereto, together with the appropriate vehicles and additives, for example, sources of fluorine, abrasives, surfactants, moisturisers, thickeners, perfuming, flavourings, preservatives, colorants, whiteners, etc.

The abrasives or polishers are used as rubbing agents, so that they remove, together with the action of the brush, the adhering residue, without damaging either the enamel or the dentine that, on occasions, is uncovered on the tooth. Traditionally calcium salts have been used, for example, calcium carbonate, tetra calcium pyrophosphate, dicalcium phosphate, calcium orthophosphate, calcium metaphosphate, or sodium salts, for example sodium metaphosphate. Due especially to the incompatibility that occurs between calcium salts and fluorides, other abrasives are now being used among which are certain silica forms. Traditionally synthetic silicas and silicates have been used that were obtained in 2 different ways, by means of a pyrogenic process or by means of a gelification process. The silicas obtained by the pyrogenic method had only thickening properties while the gelified ones behaved both as thickeners and as polishers. However, due to technological limitations, those products proved not very flexible. With the arrival of the new precipitated silicas and silicates, the precise control has become possible of the structure of these silicas through CST, Controlled Structure Technology. The result is the availability of a broad range of silicas that offer great versatility as thickeners and abrasives.

The surfactants are used in a variable concentration, according to the degree of foaming wanted, typically around 0.5% to 2% by weight with respect to the total of the formula, since, when certain limits are surpassed, they contribute to the genesis and progression of periodontopathies. Among those most used are sodium lauryl sulphate, sodium lauryl sarcosinate and tego-betaines.

The moisturisers are mandatory components in toothpaste and their mission is to maintain the initial consistency of the preparation, preventing it from setting inside the tube, and at the same time favouring the incorporation of the toothpaste in the cleaning water. The moisturisers most used at the moment are sorbitol, glycerine, polyethylenglycol and propylenglycol.

The thickeners are hydrophilic colloids the purpose of which in the toothpaste consists in avoiding the separation of the liquid components and the solids. Examples of thickeners are the gums, tragacanth, xanthan, arabic, as well as carrageen and agar—agar.

The aroma and the flavour remaining in the mouth after using a toothpaste are two features of great importance, for which it is essential that they remain unaltered in the toothpaste during its manufacture and later conservation and use. Any of the aromas can be used that are admitted by the legislation.

Sweetening or flavouring is important because it brings the taste of the preparation into harmony with the aroma. Frequently, due to the moisturiser, for example, glycerine, sorbitol, toothpastes have a faintly sweet flavour that is reinforced with sodium saccharin, in typical concentrations from 0.05% to 0.25% by weight.

Usually it is necessary to add preservatives to the formula since the moisturiser and certain mucilages favour the development of microbial flora. Among the preservatives used are those derived from benzoic acid, formol and phenol.

As colorant, any can be used of those admitted by the legislation.

Toothpaste can also contain other ingredients, depending on the properties added to those characteristic of a dentifrice. By way of example, for their properties in the elimination of proteinaceous residue deposited on rough surfaces with maximum care, proteolytic enzymes can be included, for example, papain and chymopapain, as cleansing agents and teeth whiteners. Also, they can incorporate vegetable extracts for their cosmetic and therapeutic properties for the gums and tissues of the buccal cavity. Vitamins, in particular, the antioxidant vitamins, for example, vitamin E, and other vitamins that are active in the regeneration of injured gums, for example, vitamin B5, can be included in the formula for a more complete care; equally, any liposoluble vitamin that demonstrates a beneficial action for the soft or hard tissues of the mouth could be included in the formula. For combating the occurrence of cavities, fluorinated compounds can be included, for example, sodium or potassium fluoride, sodium monofluoro-phosphate, etc. Xylitol, for its proven anti-caries properties, and because it is not metabilised by the bacteria that cause the cavity, is included more and more in toothpaste formulas.

The anticariogenic effect of a toothpaste provided by this invention (that contains olive oil), based on the removal of the cariogenic bacteria *S. mutans* [gram (+)] by the olive oil, can be improved by the incorporation in the formula of xylitol (natural acariogenic sweetener), typically in a quantity of between 0.2% and 40% by weight with respect to the total of the formula, and/or sodium fluoride (the most effective source of fluorine since it dissociates fully in solution), typically in a quantity of between 0.15% and 0.33% by weight with respect to the total of the formula. In this case, an abrasive agent, silica type, could be used to avoid calcium compounds since sodium fluoride does not allow the use of the latter.

The great non-abrasive cleansing action achieved with a toothpaste provided by this invention is independent of the source of fluorine employed, for example, sodium fluoride or sodium monofluoro-phosphate, although in this last case, calcium-based abrasives could be used. Alternatively combinations can be used of sodium monofluoro-phosphate and sodium fluoride as the source of fluorine.

In a preferred embodiment the abrasive present in the toothpaste is a new generation silica, produced by computer, of the so-called high structure silicas (CST), which the more oil absorbent they are, the less abrasive they are and, also, they have better thickening or agglutinant power. This new aspect of the absorption capacity of olive oil in high structure silicas, together with the inclusion in the formula of surfactant agents, facilitates the dispersion of the oil in the formulas, be they solid, semisolid or liquid.

A toothpaste that illustrates a toothpaste provided by this invention has the following composition:

| Component | Percentage by weight w.r.t. the total (%) |
| --- | --- |
| Olive oil | 1–70 |
| Abrasive | 10–20 |
| Moisturiser | 20–50 |
| Surfactant | 1–2 |
| Thickener | 0.5–2 |
| Sweetener | s.q. (sufficient quantity) |
| Preservative | s.q. |
| Water | s.q. for 100 |

The different products provided by the present invention, for example, toothpastes, mouthwashes, oral sprays or inhalers, chewing gum, etc., can be obtained by employing conventional techniques known by the experts in the matter.

The following examples serve to illustrate the invention and should not be considered as limiting the scope thereof.

EXAMPLE 1

Toothpaste with Olive Oil

Toothpastes were prepared whose formulas (1) and (2) are shown in Table 1, by intimately blending the different components in the appropriate quantities, by conventional methods.

Chart 1
Toothpaste with olive oil

| Component | Percentage by weight (%) | |
|---|---|---|
| | Formula 1 | Formula 2 |
| Sorbitol | 40.000 | 18.740 |
| Silica | 18.000 | 27.000 |
| Water | 15.140 | 8.000 |
| Xylitol | 10.000 | 10.000 |
| Olive oil | 5.000 | 30.000 |
| Glycerine | 5.000 | 1.000 |
| Buffer (a) | 3.200 | 1.600 |
| Aroma | 1.000 | 1.000 |
| Gum (b) | 1.000 | 1.000 |
| Titanium dioxide | 0.900 | 0.900 |
| Sodium fluoride | 0.320 | 0.320 |
| Colorant | 0.160 | 0.160 |
| Sodium saccharin | 0.130 | 0.130 |
| Preservative (c) | 0.100 | 0.100 |
| Surfactant (d) | 0.050 | 0.050 |

(a) The buffer can be, for example, that formed by citric acid/potassium citrate, or by monopotassium phosphate/tetrapotassium pyrophosphate or whatever other used in toothpaste formulas.
(b) The gum can be gum arabic, xanthan gum, carrageen or cellulose gum.
(c) The preservative can be diazolidinyl urea, imidazolidinyl urea, benzoic acid and salts thereof.
(d) Olivem ® 300 [PEG-7 olive oil, distributed by Quimibio], PEG-40 hydrogenated castor oil, and the betaine CAPB [Goldsmith].

EXAMPLE 2

Mouthwash with Olive Oil

The mouthwashes (1) and (2) whose formulas are shown in Table 2 were prepared by intimately mixing the different components in the appropriate quantities, by means of conventional techniques.

TABLE 2
Mouthwash with olive oil

| Component | Percentage by weight (%) | |
|---|---|---|
| | Formula 1 | Formula 2 |
| Water | 78.469 | 8.970 |
| Xylitol | 10.000 | 10.000 |
| Sodium saccharin | 0.030 | 0.030 |
| Olive oil | 5.000 | 40.000 |
| Glycerine | 2.000 | 31.599 |
| Aroma | 2.000 | 2.000 |
| Buffer (a) | 2.000 | 2.000 |
| Preservative (b) | 0.400 | 0.400 |
| Surfactant (c) | 0.100 | 5.000 |
| Colorant | 0.001 | 0.001 |

(a) The buffer can be, for example, that formed by citric acid/potassium citrate, or by monopotassium phosphate/tetrapotassium pyrophosphate or whatever other used in toothpaste formulas.
(b) The preservative can be diazolidinyl urea, imidazolidinyl urea, benzoic acid and salts thereof.
(c) Olivem ® 300, PEG-40 hydrogenated castor oil, CAPB.

EXAMPLE 3

Trial of Bactericidal Effectiveness of a Toothpaste Containing Olive Oil

This trial was carried out to measure the bactericidal effectiveness of a toothpaste containing olive oil. In conducting this trial the standard followed was D.G.H.M. v.01.01.81 2.2, suitably adapted.

The microorganisms on which it was tested were *Staphylococcus aureus* ATCC 6538 and *Candida albicans* ATCC 102318.

The suspension of the microorganism was prepared from cultures of 24 hours at 38° C. on Trypticase Soy Broth (TSB). The sufficiency of the number of colony-forming units (CFU)/ml ($10^8$–$10^9$) was confirmed by means of cultivation on Trypticase Soy Agar (TSA) at 37° C., 48 hours, by extraction of the corresponding decimal dilutions.

0.1 ml of the suspension of the microorganism was mixed intimately with 10 ml of the sample to be tested, for example, a toothpaste like that described in Example 1. After a contact period of 0.5, 1, 2 and 5 minutes, 0.1 ml of each of the sample/inoculant mixtures was taken and subcultured in 10 ml of TSB at 37° C. for 72 hours. The reading (+) indicates "clouding" [growth], and (−) indicates " no clouding" [absence of growth].

To check or demonstrate an eventual inhibition of growth, all the tubes that did not present clouding were reinoculated with a suspension of the microorganism (0.1 ml in TBS $10^2$–$10^3$). If clouding did not appear after a further 24 hours, the sample under test continued to be present in active form, since the inactivation was insufficient and the trial should be repeated with another medium or form of inactivation.

Table 3 shows the results obtained in the trials carried out on the different samples.

TABLE 3
Bactericidal activity of a toothpaste containing olive oil

| Inoculant | Concentration of the Inoculant (CFU/ml) | Time (min) | Concentration sample 100% (V/V) |
|---|---|---|---|
| S. aureus ATCC 6538 | $3.5 \cdot 10^8$ | 0.5 | (+) |
| | | 1 | (+) |
| | | 2 | (+) |
| | | 5 | (+) |
| C. albicans ATCC 102318 | $3.2 \cdot 10^8$ | 0.5 | (+) |
| | | 1 | (+) |
| | | 2 | (+) |
| | | 5 | (+) |

(+): Clouding (positive growth) under trial conditions, with positive actuation of the inhibitor.

The results obtained show the bactericidal capacity of the samples tested.

EXAMPLE 4

Clinical Evaluation Study of the Plaque Index and of the Gingivitis Index

This trial was carried out to evaluate effectiveness in the elimination of bacterial plaque and, in parallel, in the decrease of bleeding from the cut as a first sign of gingivitis.

Sixty (60) individuals were selected that were divided randomly into 3 subgroups of 20 persons each, the first subgroup (Group I) being required to use water for brushing teeth, the second subgroup (Group II) were to use olive oil (100%) for tooth-brushing, and the third subgroup (Group III) were to use sunflower oil (100%) for tooth-brushing [as representative of other oil types].

The individuals were kept without means of oral hygiene for 4 days, after which they received brushing instructions according to groups, 3 times a day, 3 minutes every time, for 15 days. After that time had elapsed, readings were taken of the plaque index according to the Turesky method (modification of the Quigley-Hein index with staining by eritrosine).

Also, a reading was taken of the cut bleeding index, based on the fact that gingival haemorrhage is the first sign of gingivitis. The valuation was carried out with a periodontal probe and assessed in the following way:
- 0: No bleeding
- 1: Bleeding
- 2: Bleeding+reddening
- 3: Bleeding+reddening+swelling
- 4: Bleeding+reddening+edema
- 5: Spontaneous bleeding+reddening+edema The results obtained showed, in a statistically significant manner, that Group II, which used olive oil obtained a smaller bleeding index and greater bacterial plaque elimination that the groups that used water or sunflower oil. The results demonstrated an improvement of 170% and they showed that olive oil is a positively suitable substance for achieving total elimination of plaque and combating gingivitis as the first sign of periodontal pathology.

EXAMPLE 5

Clinical Study of Effectiveness in Eliminating Supragingival Bacterial Plaque This trial was carried out to evaluate effectiveness in the elimination of supragingival bacterial plaque.

A group of 40 volunteers underwent random selection to divide them into 2 subgroups. They were instructed in habits of oral hygiene, mainly brushing with the Bass technique, for 3 minutes, twice a day and, after rinsing with water, rinsing with a specific mouthwash.

Group A (20 individuals) used:
- a commercial household toothpaste with sodium fluoride and sodium lauryl sulphate as surfactant; and
- Listerine® mouthwash with alcohol.

Group B (20 individuals) was instructed in the same techniques but instead used:
- a toothpaste specially formulated with olive oil and sodium fluoride [Example 1, Table 1, formula 1]; and
- a mouthwash specially formulated with olive oil and a surfactant (solution or aqueous dispersion) [Example 2, Table 2, formula 1].

Both groups were instructed to abstain from carrying out any form of oral hygiene for 3 days, after which (day 1) each group began to follow the above procedure.

On day 15 readings were taken of the quantity of fresh plaque, taken with a curette, of incisors, canines and pre-molars (between gingival line and incisal for vestibular) and of interproximal area.

The bacterial plaque collection in each volunteer had a standardised duration of 10 minutes.

The examiners were unaware of which of the two groups of products had been allocated to the volunteers.

The final results showed a statistically significant greater reduction in quantity of plaque (97%) in the group of volunteers that used toothpaste and mouthwash with olive oil, in comparison with a conventional toothpaste with sodium fluoride and sodium lauryl sulphate as surfactant (60% plaque reduction).

The invention claimed is:

1. A toothpaste for reducing bacterial plaque comprising anticariogenic effective amounts of olive oil, xylitol and a source of fluoride, wherein said toothpaste does not contain parsley oil.

2. The toothpaste according to claim 1 wherein said toothpaste comprises xylitol in an amount of 0.2 to 40% by weight and sodium fluoride in an amount of 0.15 to 0.33% by weight.

3. The toothpaste according to any one of claims 1 and 2, wherein said toothpaste additionally contains high structure silica.

4. A method for improving the anticariogenic effect of a toothpaste formulation comprising olive oil and a source of fluoride that comprises adding a sufficient amount of xylitol to said formulation to provide a decrease in plaque formulation in comparison to that obtained with a toothpaste formulation which is substantially free of said xylitol wherein said toothpaste formulation does not contain parsley oil.

5. The method according to claim 4, wherein said toothpaste formulation further comprises at least one high structure silica added as an abrasive.

* * * * *